(12) United States Patent
Hansen et al.

(10) Patent No.: US 10,047,331 B2
(45) Date of Patent: Aug. 14, 2018

(54) TRAY, A SYSTEM AND A METHOD FOR MONITORING AND CULTURING OF A CELL CULTURE

(71) Applicant: UNISENSE FERTILITECH A/S, Aarhus N (DK)

(72) Inventors: Jonas Lerche Hansen, Aarhus (DK); Niels B. Ramsing, Aarhus (DK); Søren Porsgaard, Aarhus (DK); Holger Søe Plougsgaard, Ega (DK); Mai Faurschou Isaksen, Høejbjerg (DK)

(73) Assignee: UNISENSE FERTILITECH A/S, Aarhus N (DK)

( * ) Notice: Subject to any disclaimer, the term of this patent is extended or adjusted under 35 U.S.C. 154(b) by 0 days.

(21) Appl. No.: 14/772,663

(22) PCT Filed: Mar. 13, 2014

(86) PCT No.: PCT/EP2014/054968
§ 371 (c)(1),
(2) Date: Sep. 3, 2015

(87) PCT Pub. No.: WO2014/140181
PCT Pub. Date: Sep. 18, 2014

(65) Prior Publication Data
US 2016/0017267 A1    Jan. 21, 2016

Related U.S. Application Data

(60) Provisional application No. 61/799,836, filed on Mar. 15, 2013.

(30) Foreign Application Priority Data

Mar. 19, 2013   (EP) ..................... 13159965

(51) Int. Cl.
*C12M 1/34*    (2006.01)
*C12M 3/00*    (2006.01)
(Continued)

(52) U.S. Cl.
CPC ........... *C12M 23/12* (2013.01); *B01L 3/5085* (2013.01); *C12M 21/06* (2013.01); *C12M 23/02* (2013.01);
(Continued)

(58) Field of Classification Search
CPC ..... B01L 2200/0668; B01L 2300/0654; B01L 2300/0829; B01L 2300/0851;
(Continued)

(56) References Cited

U.S. PATENT DOCUMENTS 4,956,150 A * 9/1990 Henry ................. B01L 3/5085
356/244
5,171,995 A   12/1992 Gast et al.
(Continued)

FOREIGN PATENT DOCUMENTS

EP       0963790 A2    12/1992
WO    2009/003487 A2    1/2009

OTHER PUBLICATIONS

International Search Report and Written Opinion of the International Searching Authority for PCT/EP2014/054968, dated Aug. 13, 2014 (dated Aug. 13, 2014); the whole document.
(Continued)

*Primary Examiner* — Nathan A Bowers
*Assistant Examiner* — Lydia Edwards
(74) *Attorney, Agent, or Firm* — Steptoe & Johnson LLP

(57) ABSTRACT

A tray (100; 400; 500; 600) for accommodating a cell culture (101), such as an embryo, for use during culturing thereof and for optical monitoring of the cell culture, e.g. during in vitro fertilization comprises a carrier structure (104;404;
(Continued)

504;604) defining at least one accommodating zone (102; 402; 502; 602) for accommodating the cell culture. At least one focal lens (110; 410; 510; 610), notably a numerical aperture increasing lens is integrally formed with the carrier structure to facilitate monitoring of the cell culture through the carrier structure. A diameter of the focal lens may exceed a diameter of the at least one accommodating zone. The focal lens may be integrally molded with the carrier structure from a thermoplastic material.

11 Claims, 14 Drawing Sheets

(51) Int. Cl.
*C12M 1/32* (2006.01)
*B01L 3/00* (2006.01)
*C12M 1/00* (2006.01)
*G01N 33/50* (2006.01)

(52) U.S. Cl.
CPC ......... *C12M 41/36* (2013.01); *G01N 33/5005* (2013.01); *B01L 2200/0668* (2013.01); *B01L 2300/0654* (2013.01); *B01L 2300/0829* (2013.01); *B01L 2300/0851* (2013.01)

(58) Field of Classification Search
CPC ..... B01L 3/5085; C12M 21/06; C12M 23/12; G01N 33/5008
See application file for complete search history.

(56) References Cited

U.S. PATENT DOCUMENTS

| 2003/0052002 A1* | 3/2003 | Vogel | G01N 33/48728 204/403.01 |
| 2011/0141463 A1* | 6/2011 | Chikamatsu | G01N 21/956 356/237.5 |
| 2011/0165609 A1* | 7/2011 | Ramsing | C12M 21/06 435/29 |

OTHER PUBLICATIONS

European Search Report for EP 13159965, dated Aug. 27, 2013 (dated Aug. 27, 2013), the whole document.

* cited by examiner

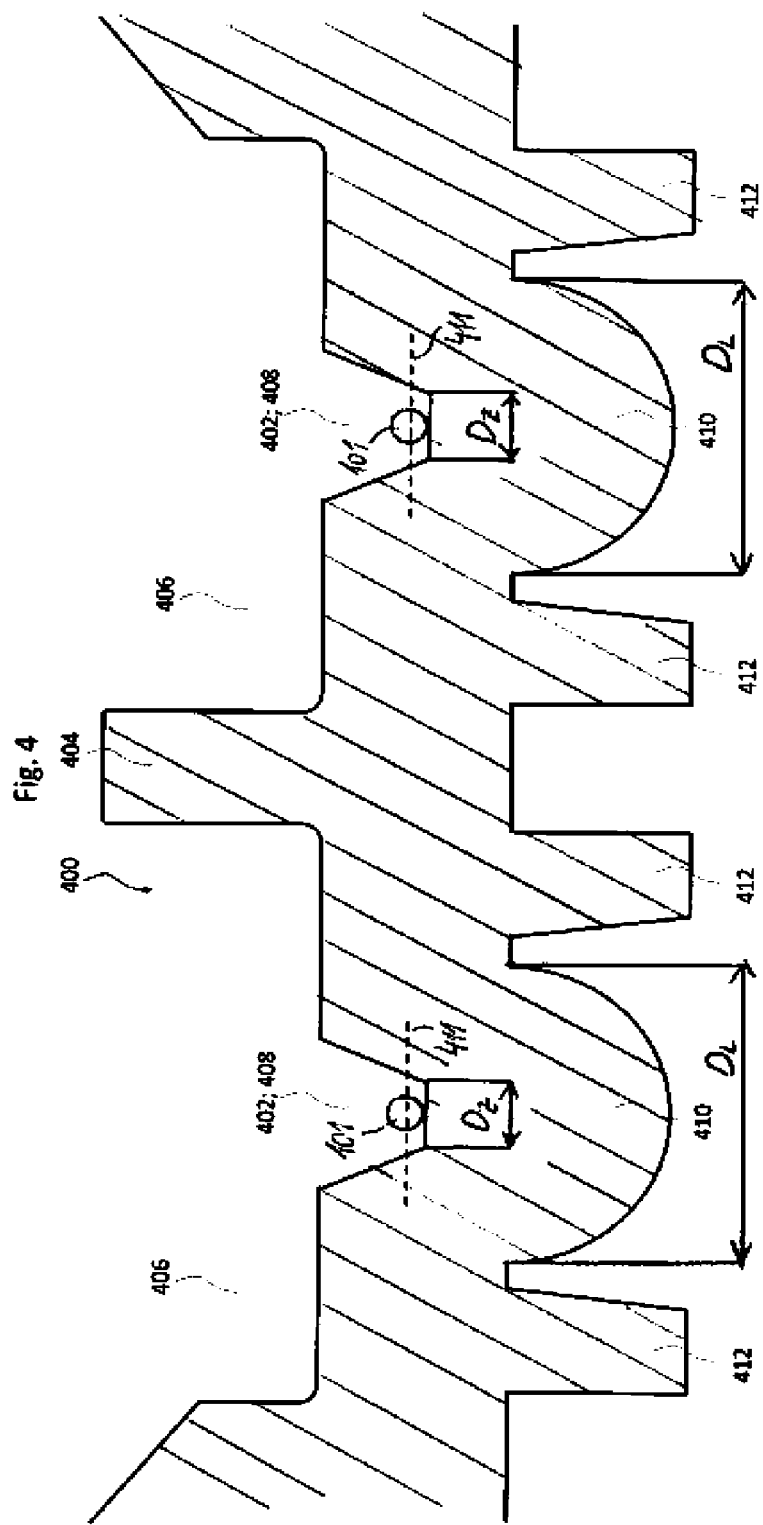

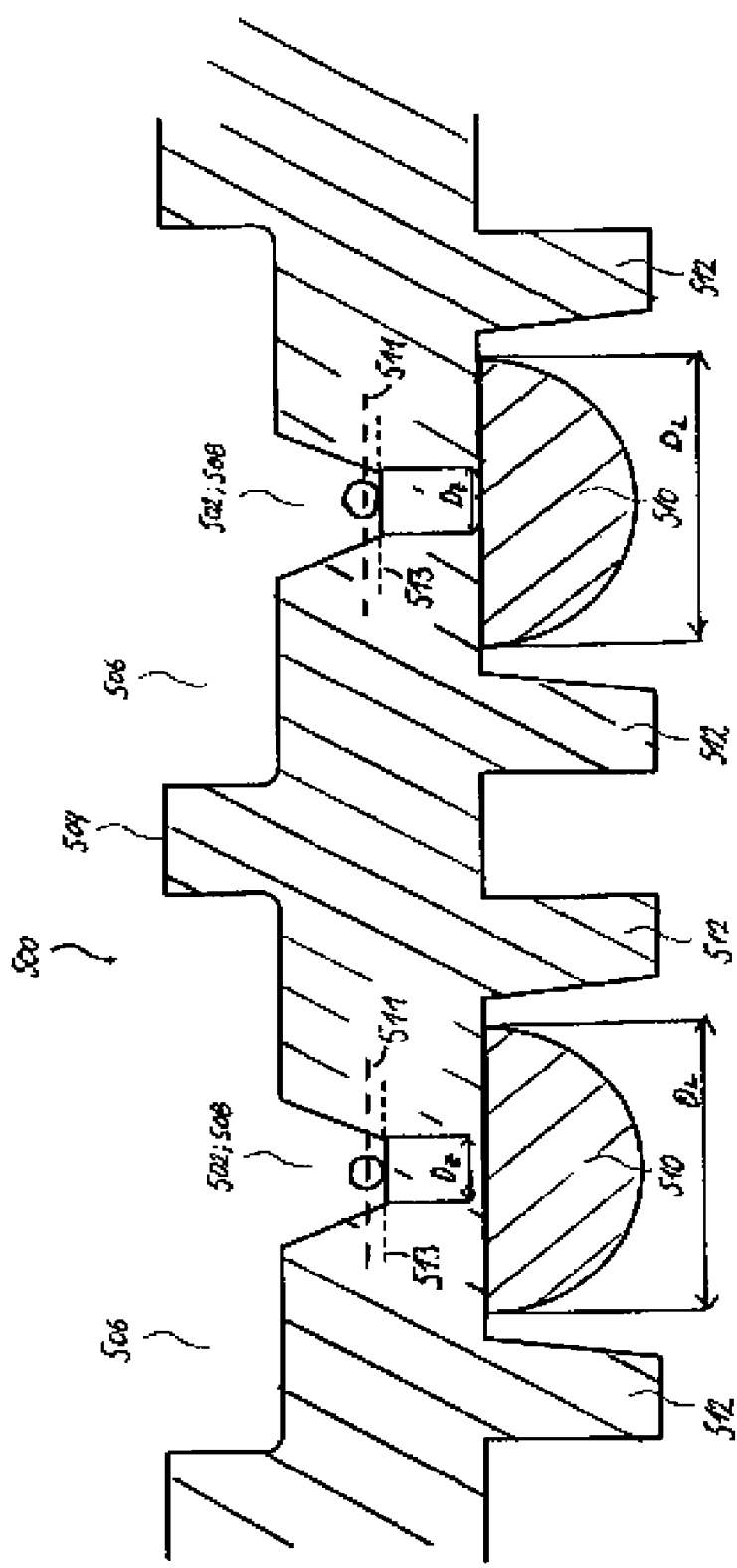

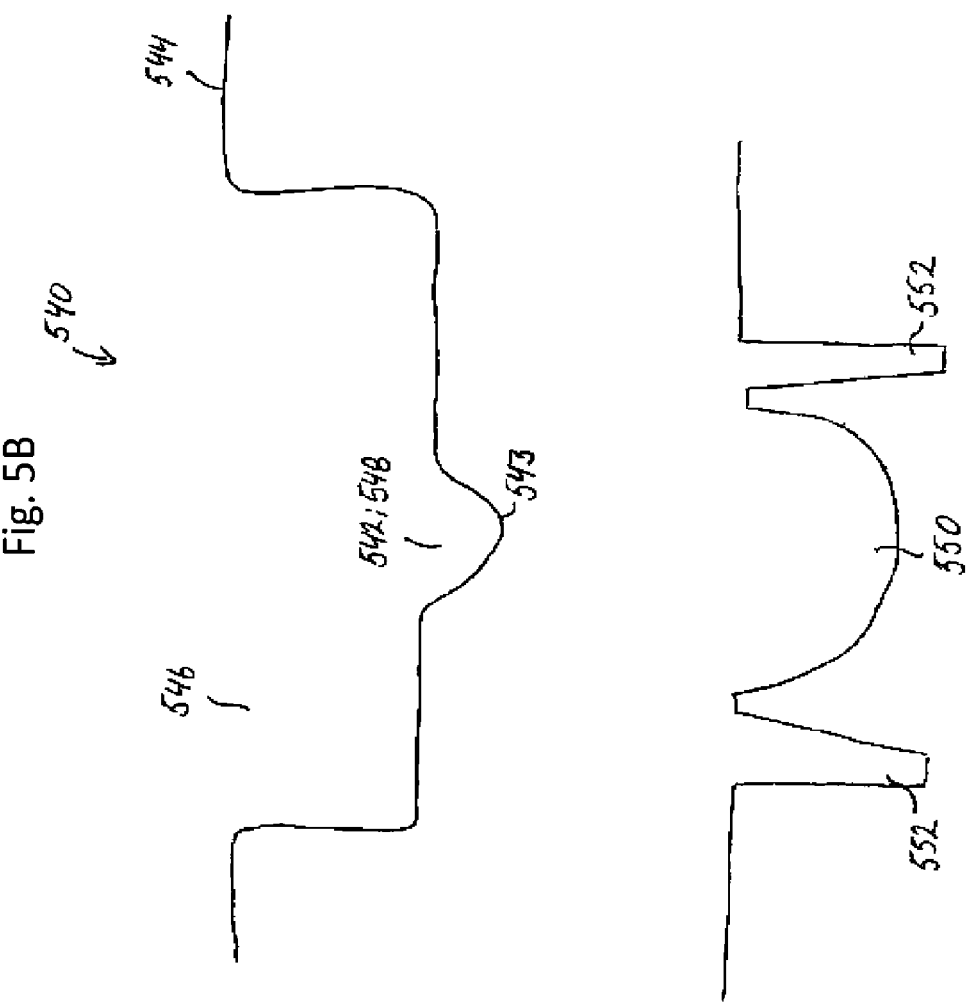

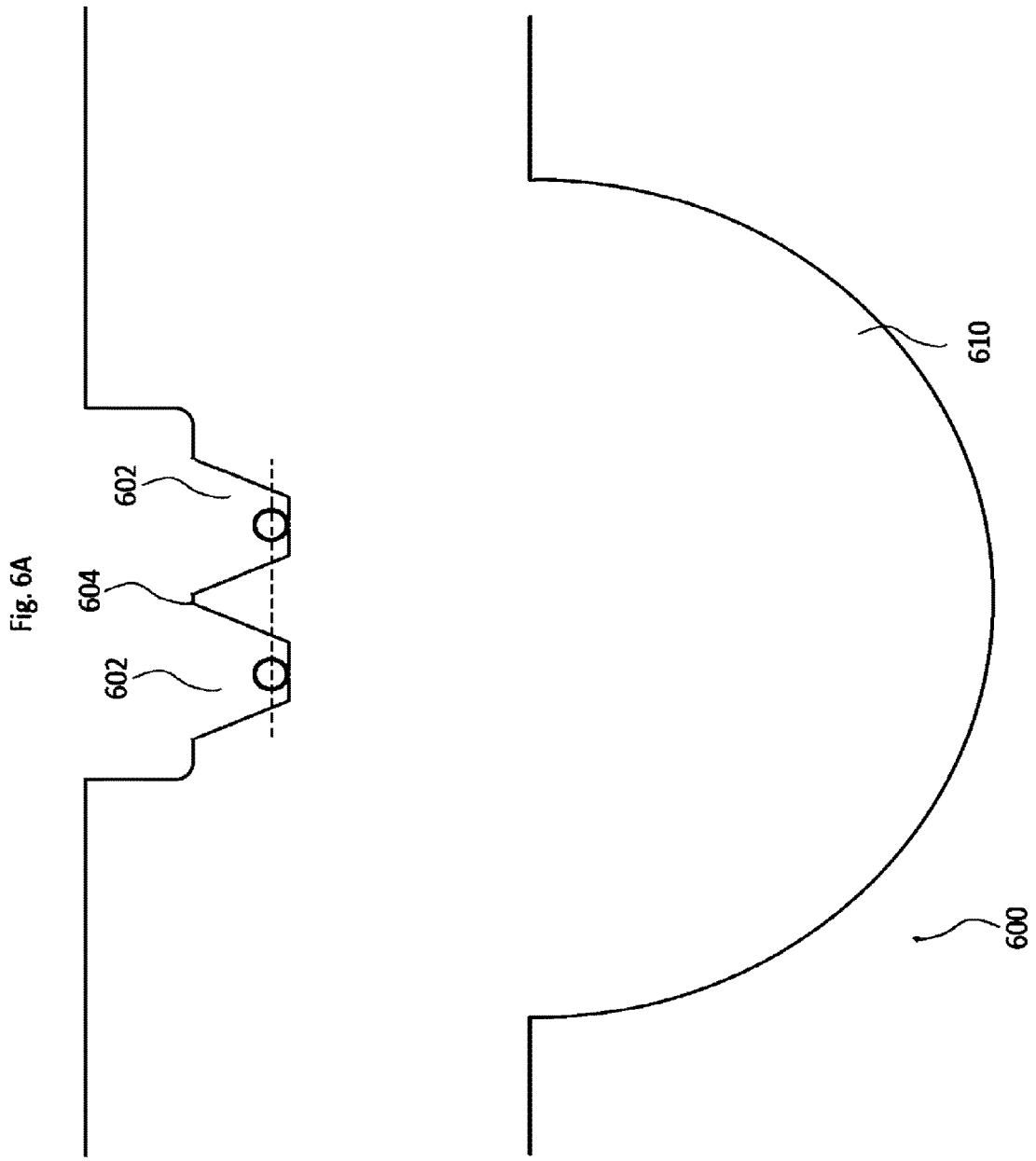

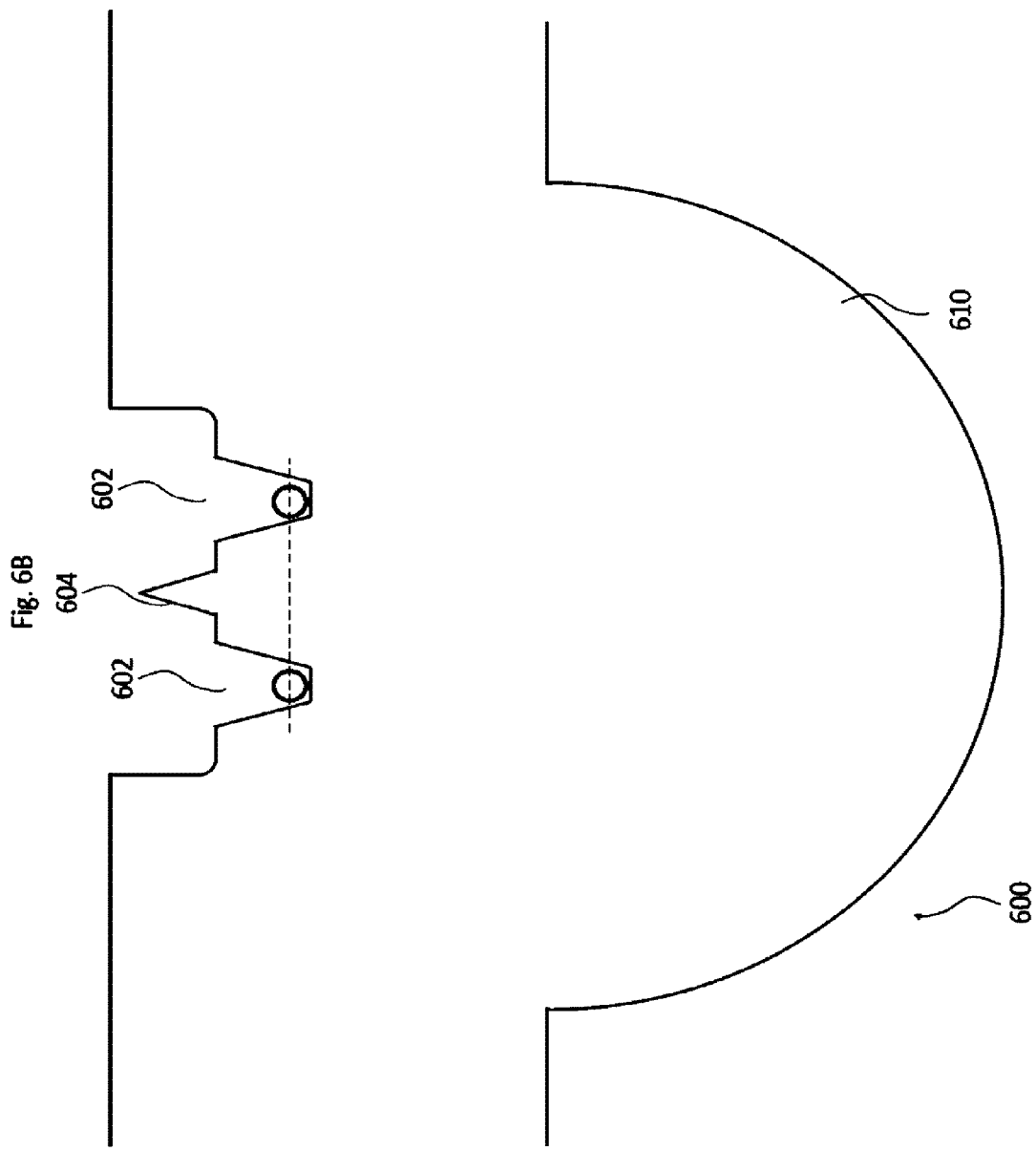

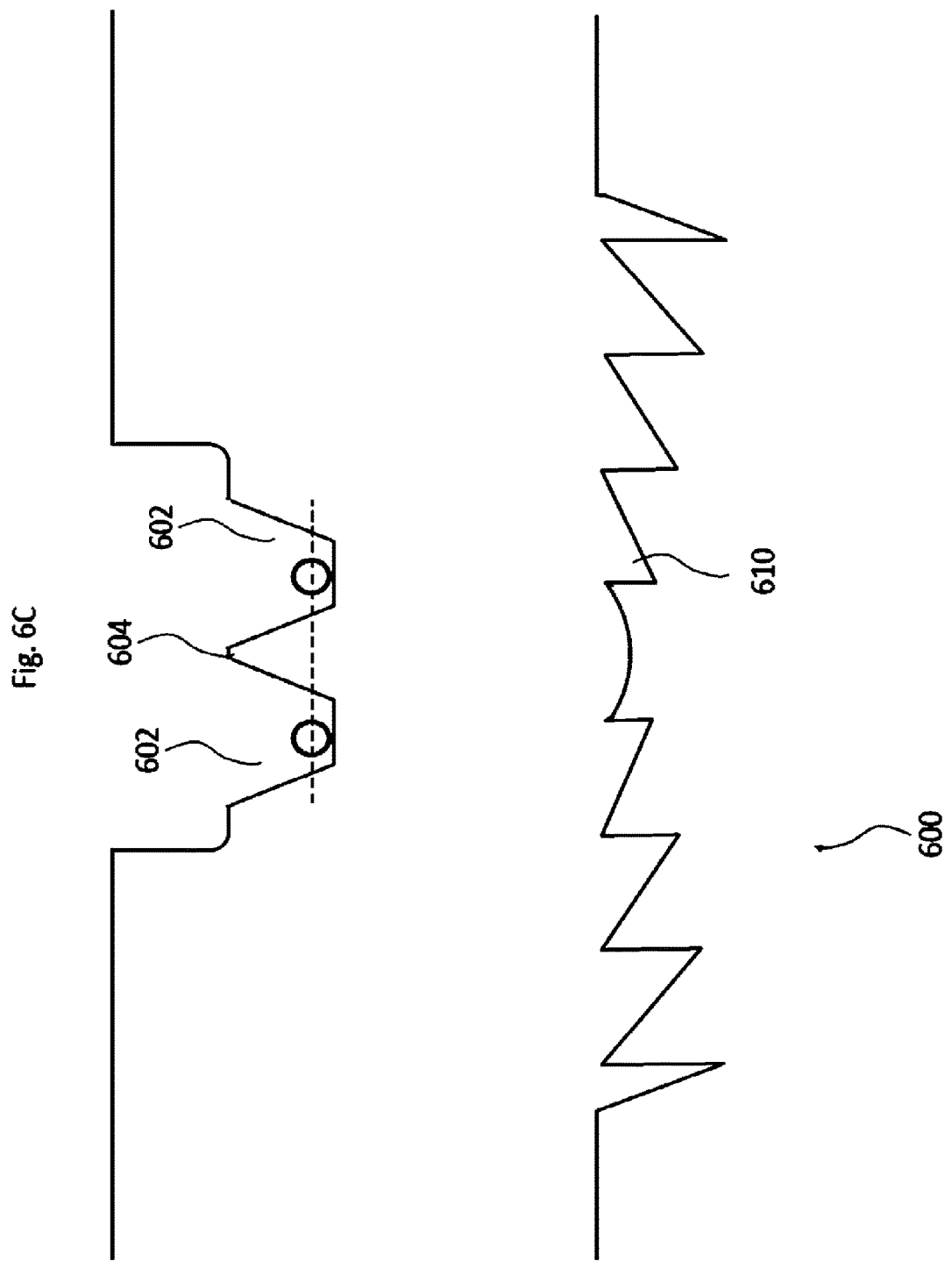

TRAY, A SYSTEM AND A METHOD FOR MONITORING AND CULTURING OF A CELL CULTURE

CLAIM FOR PRIORITY

This application claims priority under 35 USC 371 to International Application No. PCT/EP2014/054968, filed on Mar. 13, 2014, which claims priority to U.S. Patent Application No. 61/799,836, which was filed on Mar. 15, 2013, and European Patent Application No. 13159965.6, filed Mar. 19, 2013, each of which is hereby incorporated by reference in its entirety.

TECHNICAL FIELD

The present invention relates to a device, referred herein to as a tray, a system and a method for facilitating monitoring and/or culturing of microscopic objects, notably cell cultures, such as embryos as part of an in vitro fertilization (IVF). In one embodiment, the invention provides high resolution images of developing embryos with superior detail due to increased numerical aperture. In another embodiment, the invention aims at facilitating handling and secure identification of embryos during automated digital imaging and time-lapse microscopy.

BACKGROUND OF THE INVENTION

In microscopy of live eukaryotic and prokaryotic cell cultures, including oocytes and embryos during, e.g., IVF treatment, it is generally desirable to reduce stress imposed on the cell cultures during handling thereof.

The diameter of early human embryos is about ⅛ mm (approximately 120 μm) with a density slightly higher than their growth medium. Positioning embryos accurately in media droplets is difficult, and handling may easily disturb their position. When applying Embryo Transfer (ET) techniques, such as IVF (In Vitro Fertilization) and related techniques, in vitro culturing of the developing embryo is carried out for a period of days before transfer of selected embryos back to uterus of the recipient patient. Even under ideal growth conditions, selection criteria are needed as a tool to choose the most viable embryos for transfer as most embryos have genetic defects (e.g. aneuploidy) that prevent them from developing to healthy infants. Assessment of the viability of an embryo will determine the embryos' suitability for transfer. In traditional IVF, embryo assessment is limited to a more or less subjective grading based on morphological criteria. As the embryo development is a dynamic and gradual process it is most readily and comprehensively evaluated by a succession of images such as those provided by Time-Lapse (TL) microscopy. Automation is essential when capturing images at defined time intervals of numerous growing embryos and is a prerequisite for clinical use of TL imaging for embryo viability assessment. At a practical level, precise positioning for microscopy facilitates assessment of the viability of an embryo based on automated time-lapse imaging.

Therefore, a need exists for a fast, simple and non-disturbing method, system and device for facilitating and automating morphological evaluation.

International patent publication No. WO 2009/003487 discloses a device for use during monitoring and/or culturing of microscopic objects. The device disclosed therein addresses issues related to providing stable incubation conditions, and to facilitating handling of the objects, including automated handling.

A microscope is normally used for optically monitoring cell cultures, such as embryos. Digital image acquisition and analysis equipment is typically applied to assist a human examiner in deriving appropriate information as needed from the acquired microscope images. In conventional microscopy applications, such as those used in IVF, a certain distance usually exists between an optical lens of a microscope and the cell culture to be monitored, the distance being given by the thickness of a tray accommodating the cell culture, insulating and heat conducting elements providing a thermostatic environment and sealing elements to maintain a controlled atmosphere and air gaps between the aforementioned elements to allow for mechanical movement and exchange of the cell cultures being monitored.

The quality of the captured microscope images evidently plays a role for the quality of the analysis that can be made on the basis of the images. One way of increasing image quality is to increase the pixel resolution of the digital camera equipment, which captures the images. However, increasing camera resolution beyond the resolution of the optical system will not provide additional detail but only magnify the image reproducing the blurry outlines of the visible components.

The resolution of the employed lens system can be described by the required distance between two tiny objects for them to be perceived as separate objects and not part of the same elongated object (cf. descriptions of optical systems, Airy disk etc.): If two objects imaged by an optical system are separated by an angle small enough that their Airy disks on the optical systems detector (i.e. camera) start overlapping, the objects can not be clearly separated any more in the image, and they start blurring together. Two objects are said to be just resolved when the maximum of the first Airy pattern falls on top of the first minimum of the second Airy pattern (the Rayleigh criterion). Therefore the smallest separation two objects can have before they significantly blur together is approximated by the size of the Airy disk:

$$h = 0.61 \lambda / NA$$

where $\lambda$ is the wavelength of the light and NA is the numerical aperture given by:

$$NA = n^* \sin(e)$$

Where n is the refractive index and $\theta$ is the half-angle of the maximum light cone collected by the optical system.

One way of increasing the optical resolution (i.e. decreasing h) would be to reduce the wavelength of the light used (e.g. change from red to green or preferably blue light or even most preferably to UV light). However, short wavelength light has higher energy and has been shown to be far more phototoxic to living organisms than long wavelength light. For clinical applications it is thus advisable to use only long wavelength red light to minimize any potential damage to living organisms.

Another way of increasing image quality (i.e. decreasing h) is to increase the numerical aperture of the optical system. This can be accomplished by increasing the refractive index (e.g. by liquid immersion microscopy) or by increasing the half-angle of the light cone collected by the microscope objective. Liquid immersion is impractical in an automated system with moving parts that mechanically change between acquiring images of different cells/embryos. Even in a stationary system cleaning and handling is more complicated when using liquid immersion and there is a larger potential for contamination.

Increasing the acceptance angle for the light cone of the collected light is usually accomplished by positioning the objective closer to the investigated object while increasing the magnification of the objective. High magnification objectives with high numerical aperture thus require close proximity between the observed object and the position of the microscope lens. However, it is not always possible to place the objective close to the living cells for instance if the observed object must be mechanically exchanged with other similar objects and if the object must be in a protected stable environment (e.g. in a thermostatic holder with direct heat transfer to the culture vessel). Cultivation systems that maintain a thermostatic environment and a controlled atmosphere optimized for embryo development often require a minimal distance/separation between the living cells and the microscope objective as mentioned above.

Increasing the diameter of the optical lens to increase the acceptance angle of incident light is generally prohibitively expensive. The numerical aperture of an optical system based on standard microscope elements (objective and tubal lenses and camera lenses) can thus not be increased infinitely, and the requirement to maintain a stable environment for embryo development/cell culture may further limit the optical resolution that can be achieved. The optical resolution and hence image quality is therefore limited.

DESCRIPTION OF THE INVENTION

On the above background, it is an object of embodiments of the invention to provide a tray for accommodating cell cultures during culturing thereof, and a system and a method for handling cell cultures during culturing thereof, which increase quality of images of cell cultures, such as embryos, captured through a microscope lens. It is a further object of embodiments of the invention to provide a tray and system, the manufacture and operation of which is inexpensive. It is a further object of embodiments of the invention to provide a robust and resilient system where the likelihood of unintended mix-up of the cell cultures/embryos is reduced and were correct re-positioning of the cell culture/embryos between consecutive frames is less critical.

In a first aspect, the invention provides a tray for accommodating a cell culture for use during culturing thereof and/or for optical monitoring of the cell culture, the tray comprising a carrier structure defining at least one accommodating zone for accommodating the cell culture, wherein the carrier structure comprises at least one focal lens, which is integrally formed with or bonded to the carrier structure, the at least one focal lens being arranged to collect light rays emanating from the at least one accommodating zone so as to facilitate monitoring of the at least one accommodating zone, notably of the cell culture accommodated therein, through the focal lens and the carrier structure.

It will hence be appreciated that the present invention presents a system whereby part of the magnifying optical system that conventionally resides in the microscope objective is incorporated in the culture vessel itself and thus effectively achieving an increased working distance between the monitored object (living cell or embryo) and the objective for a given magnification and image quality, that cannot be achieved with traditional long working distance objectives.

The focal lens is provided to increase the optical resolution of images acquired through the focal lens and carrier structure when observing the at least one accommodating zone by increasing the numerical aperture of the combined optical system. In other words, the at least one focal lens is arranged to increase the numerical aperture of an optical system for inspecting the at least one accommodating zone through the carrier structure. Thanks to the at least one focal lens, the quality of the captured microscope images is improved in the sense that the image quality is not restricted to the properties of a microscope lens or any other external lens through which the images are captured. Moreover, given that a certain distance usually exists between an optical lens of a microscope and the cell culture to be monitored due to the presence of the tray accommodating the cell culture and of insulating and sealing elements and air gaps between the aforementioned elements, the focal lens of the tray of the present invention enables the collection of light rays from a focal plane extending at or through the cell culture by means of a lens having dimensions which are considerably smaller than a remote lens arranged at a distance of, e.g. 8-10 mm from the tray.

In the present context, the term focal lens should be understood to encompass any transparent structure with at least one curved or symmetrically structured surface for providing a concentration of light rays. A focal lens is thus a term for any type of convex lens (e.g. biconvex, plano-convex or other lenses with a positive meniscus). A focal lens is a converging lens, and the term does not apply to concave diverging lenses, but it is not restricted to spherical lenses. The lens may be a spherical or an aspherical lens or a Fresnel lens or another type of converging lens. It will be understood that the focal lens is provided to increase a numerical aperture of the carrier structure for monitoring the at least one accommodating zone.

In order to ensure appropriate magnification of the entire cell structure in the accommodating zone with limited distortion, a diameter of the focal lens preferably exceeds a diameter of the at least one accommodating zone. For example, the focal lens may define a first diameter $D_L$ at its interface with a surface of the carrier structure. The accommodating zone, formed e.g. as a well in depression in the carrier structure, may define a second diameter $D_Z$. In a preferred embodiment of the invention, the accommodating zone diameter $D_Z$ is smaller than the lens diameter $D_L$ in order to ensure that the lens provides sufficient magnification of the entire surface area of the accommodating zone, e.g. at the bottom of the well. In a more preferred embodiment of the invention the accommodating zone diameter is less than half the lens diameter $D_L$. In a most preferred embodiment of the invention the accommodating zone diameter is less than one fourth of the lens diameter $D_L$. In some embodiments the lens is hemispherical in which case the lens diameter $D_L$ is the radius of the hemisphere. In other embodiments the lens surface is a part of a larger hemisphere in which case the radius of the curvature of the lens surface should preferably exceed the diameter of the accommodating zone though the lens diameter itself may be less than twice the diameter of the accommodating zone.

The accommodating zone may be provided as a well in the carrier structure. For example, a depression may be formed in the carrier structure to define the well. In the depression an indent may be provided for accommodating the cell culture. Alternatively, the accommodating zone may be provided as a structure projecting from a surface of the carrier structure. In another embodiment the accommodating structure is in the same plane as the surface of the carrier but surrounded by a protruding wall. The shape of the accommodating zone may be circular, but could as well be rectangular, square, hexagonal etc. However, delineation of the accommodating zone may ensure that the cells/embryos are positioned correctly with respect to the focal lens to ensure image quality. The accommodating zone may be further surrounded by walls, or constitute depressions, wells etc. to reduce the chance that the embryos are accidentally displaced by vibrations or during handling.

The cell culture normally is a structure having a diameter not exceeding 2 mm, such as at most 1 mm, such as less than 500 µm, such as less than 200 µm. The accommodating zone preferably has a diameter of about 1.1 to 10 times the diameter of the cell culture, preferably 1.5 to 3 times the diameter of the cell culture, so that the position of the cell culture within the accommodating zone is well defined. The diameter of the accommodating zone is preferably between 100 and 600 µm, such as between 150 and 500 µm or between 200 and 300 µm. The accommodating zone preferably has a substantially planar surface for supporting the cell culture, but may have a curved surface to enable the cell culture to roll into the middle of the accommodating structure. In some instances this is a preferred embodiment, however this may necessitate adaptation of the lens surface to accommodate for any optical distortion induced by a curved bottom surface as the curved surface between medium and support with a different refractive index will act as an optical lens element. In embodiments, in which the accommodating zone comprises a well formed, e.g. by a depression and/or an indent in the carrier structure, the height of the indent or well may be between 0.1 and 5 mm, such as between 0.1 and 1 mm, such as between 0.1 and 0.4 mm.

A bottom wall formed by the carrier structure at the accommodating zone preferably has a thickness of between 0.2 and 5 mm, such as between 0.2 and 2 mm, such as between 0.5 and 1.5 mm, such as between 0.6 and 1.2 mm. The carrier structure is preferably transparent. At least that part of the carrier structure forming a bottom wall at the accommodating zone should preferably be transparent.

In one particularly preferred embodiment, the at least one focal lens is formed from and integrally moulded with the material forming the carrier structure at the at least one accommodating zone. The material may advantageously be a plastics material, preferably a thermoplastic material, such as polystyrene or polycarbonate. By integrally moulding the carrier structure and the focal lens together from a single piece of material, an inexpensive tray is provided, which may disposed of after use. Accordingly, the burden of cleaning and sterilizing the tray after use may be eliminated. Integrally moulding of the focal lens and carrier structure from a single piece of material is in particular rendered possible in embodiments, in which a diameter of the focal lens exceeds a diameter of the accommodating zone, such as for example in embodiments, in which the diameter of the focal lens exceeds 0.8 mm. At such lens diameters, achievable manufacturing tolerances are possible which do not affect the optical properties of the lens to an unsatisfactory degree.

As an alternative to integrally moulding the carrier structure and the focal lens from a single material, the at least one focal lens may be provided as a separate element, which is embedded in or bonded to the carrier structure. The focal lens may be formed from a material other than the material forming the carrier structure at the at least one accommodating zone, or it may be formed from the same material as the material forming the carrier structure at the least one accommodating zone.

In one embodiment of the invention, the at least one accommodating zone comprises a plurality of accommodating zones, and each one of the at least one focal lens is sized to cover a single accommodating zone only. Hence, the number of focal lenses is equal to the number of accommodating zones. In another embodiment, the at least one accommodating zone comprises a plurality of accommodating zones, wherein a single one of the at least one focal lens is sized to cover at least two of said accommodating zones. In either embodiment, a diameter of the focal lens is preferably sized to exceed a diameter of the accommodating zone. For example, the diameter of the accommodating zone may be between 0.1 and 0.5 mm, and the diameter of the lens may be at least 0.8 mm such as between 1 and 2 mm.

In a second aspect, the present invention provides a system for culturing of a cell culture and for optical monitoring thereof during culturing of the cell culture, comprising a tray according to the first aspect of the invention as claimed and described herein, and an optical inspecting unit arranged to enable or facilitate optical monitoring of the cell culture accommodated in the at least one accommodating zone of the carrier structure.

The system according to the second aspect of the invention may include a culturing chamber, such as an incubating chamber, and a control system for maintaining a controlled environment (e.g. thermostasis and defined atmosphere) in the culturing chamber. The controlled environment may e.g. be controlled to maintain a predetermined temperature and a predetermined concentration of one or more specific gasses, such as oxygen and carbon dioxide in the culturing chamber. Further, the system may be arranged to keep the culturing chamber at darkness, i.e. to essentially prevent surrounding light from entering the culturing chamber. A light source controlled by the control system may be provided to illuminate the culturing chamber or at least the accommodating zone at points in time, at which it is desirable to acquire an image of the cell culture, and only for the duration to the time it takes to acquire said image The optical inspecting unit may advantageously comprise a fixed optical system using microscope components (e.g. objectives, auxiliary lenses and camera unit) or other suitable device for further magnifying an image of the cell culture visible through the focal lens of the tray. A camera may further be included in the optical inspecting unit for capturing images at distinct points in time to monitor changes of the cell culture occurring over time. The system may further comprise an appropriately programmed computer for performing image analysis and/or for displaying the captured images to an operator.

The system according to the invention may comprise more than one inspecting unit, including more than one camera for inspecting respective accommodating zones of the tray. Alternatively, one single inspecting unit may be provided. In one embodiment different inspecting units may be positioned to monitor different accommodating zones individually. In another embodiment different inspection units may be positioned to monitor the same accommodating zone from different angles, thus providing additional basis for a three dimensional interpretation of the contained cell culture. A multidimensional representation may thus be derived by following changes to the 3D structure of the cell culture over time. The inspecting unit may be stationary, i.e. immobilized, or movement elements may be provided for displacing the inspecting unit and/or the tray (and hence the cell cultures in the at least one accommodating zone) relative to each other. The optical inspecting unit may be arranged to provide images of the cell culture in the accommodating zone in a plurality of focal planes at various distances from a bottom surface of the accommodating zone, thus representing another way to obtain a three dimensional interpretation of the cell culture structure. A multidimensional representation may thus be derived by following changes to the 3D structure of the cell culture over time.

A preferred embodiment further encompass motorized means for intermittently/sequentially positioning at least two, such as 3 or more, trays according to the first aspect of the invention as claimed and described herein in the optimal position for acquisition of images by a stationary optical inspection unit.

In another preferred embodiment further encompass means for intermittently/sequentially positioning the optical inspection unit in the optimal position for acquisition of images of at least two, such as 3 or more, stationary trays according to the first aspect of the invention as claimed and described herein.

In a further independent aspect the invention provides a method for culturing of a cell culture and for optical monitoring thereof during culturing of the cell culture, comprising:
  providing a tray, such as a tray according to the first aspect of the invention as claimed and described herein, for accommodating the cell culture, the tray comprising a carrier structure defining at least accommodating zone for accommodating the cell culture, wherein the carrier structure comprises at least one focal lens, which is integrally formed with or bonded to the carrier structure, and wherein the at least one focal lens is arranged to collect light rays emanating from the at least one accommodating zone so as to facilitate monitoring of the cell culture through the focal lens and the carrier structure;
  providing the cell culture in the at least one accommodating zone;
  providing at least one optical inspecting unit arranged to enable or facilitate monitoring of the cell culture accommodated in the at least one accommodating zone of the carrier structure.

In case the optical inspecting unit comprises at least one camera unit, the method according to the invention may further comprises acquiring, by means of the camera unit, a plurality of images of the cell culture accommodated in the at least one accommodating zone through the at least one focal lens, the plurality of images being acquired at different points in time. Accordingly, cellular changes, such as the development of an embryo over time may be monitored.

The cell culture may be preserved in a fluid accommodated in the accommodating zone along with the cell culture. A ratio of a refraction index of the fluid and a refraction index of the material forming the carrier structure at the accommodating zone is preferably between 0.5 and 2. By selecting a refraction index of the fluid or alternatively the material of the carrier to minimize the difference in refractive index of the two components, the effect of optical disturbances induced by the transition when light passes from the carrier to the medium may be reduced or even eliminated.

Further features and dimensions of the tray (except the focal lens) according to the present invention and its use are disclosed in Applicants' prior publication No. WO 2009/003487, which is hereby incorporated by reference.

DESCRIPTION OF EMBODIMENTS OF THE INVENTION

The invention will now be further described with reference to the accompanying drawings, in which FIG. 1 shows a top view of an embodiment of a tray according to the invention; In this particular representation 100: Overall dimensions are 25×75 mm, 106 are 12 large wells with a diameter of 4 mm, 102 are small microwells that are depressions within the larger wells. The microwells are 0.3 mm in diameter and 0.3 mm deep.

Figure 1:
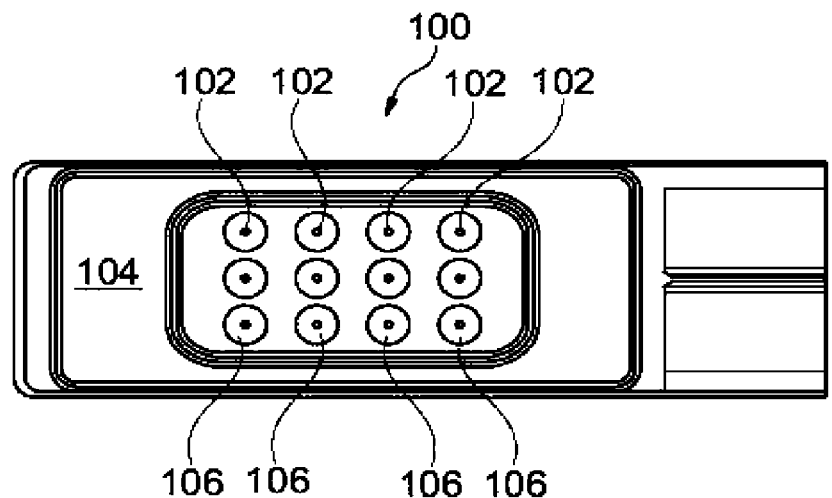

FIGS. 4 and 5A and 5B show cross-sections of a first and a second embodiment of a tray according to the invention; the first embodiment in FIG. 4 includes an integral focal lens 410 which collects light emanating from the cell culture in the microwell 402. The second embodiment in FIG. 5A is an equivalent design with attached focal lenses, 510, positioned beneath the cell cultures in the accommodating wells 502. FIG. 5B shows an alternative configuration of a microwell being concavely curved for accommodation of a cell culture.

FIGS. 6A-6C illustrate further embodiments of a tray according to the invention, which comprise multiple accommodating zones 602, optionally separated by barriers projecting from the surface 604. The multiple accommodating zones of each embodiment can be monitored through a common focal lens 610.

Figure 7:
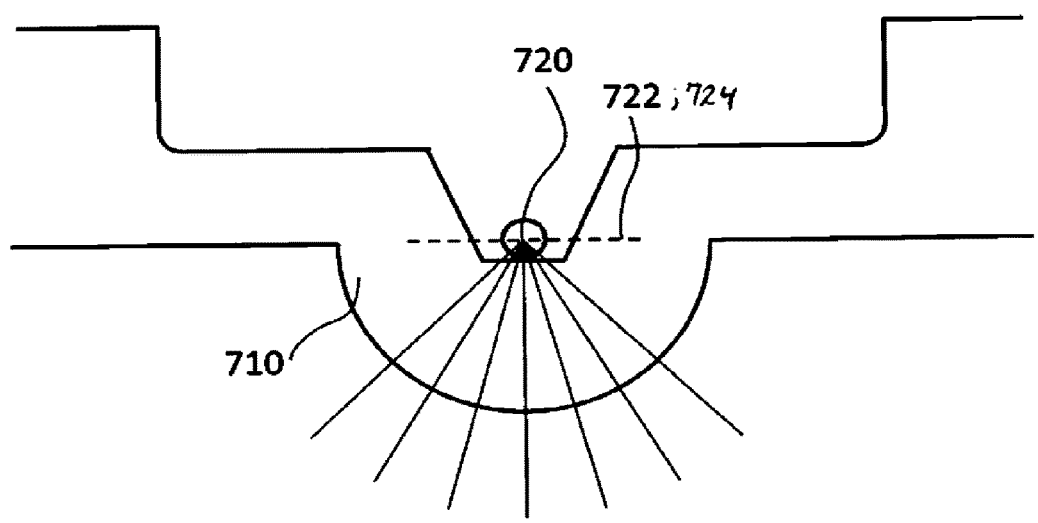
Figure 8A:
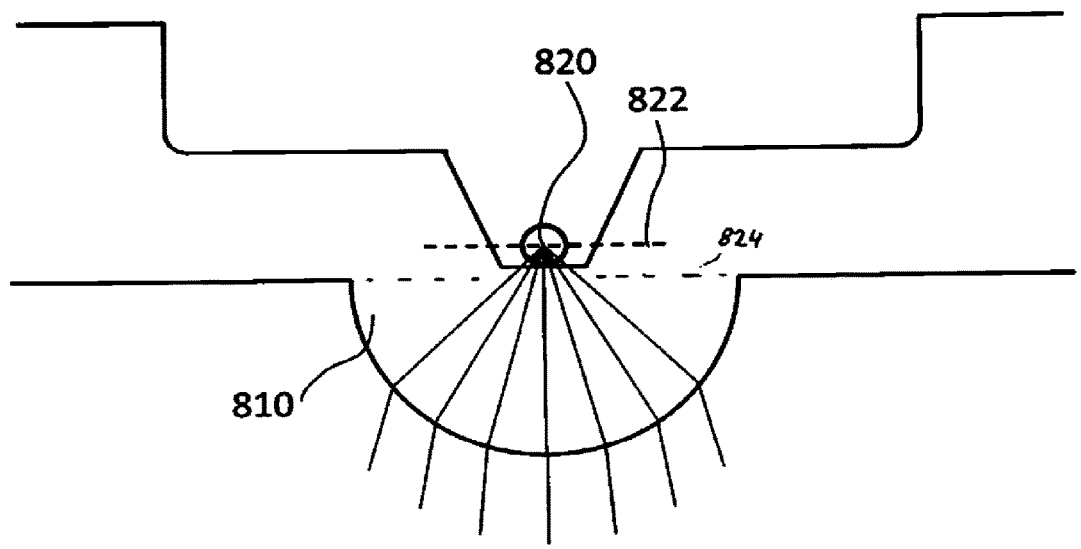
Figure 8B:
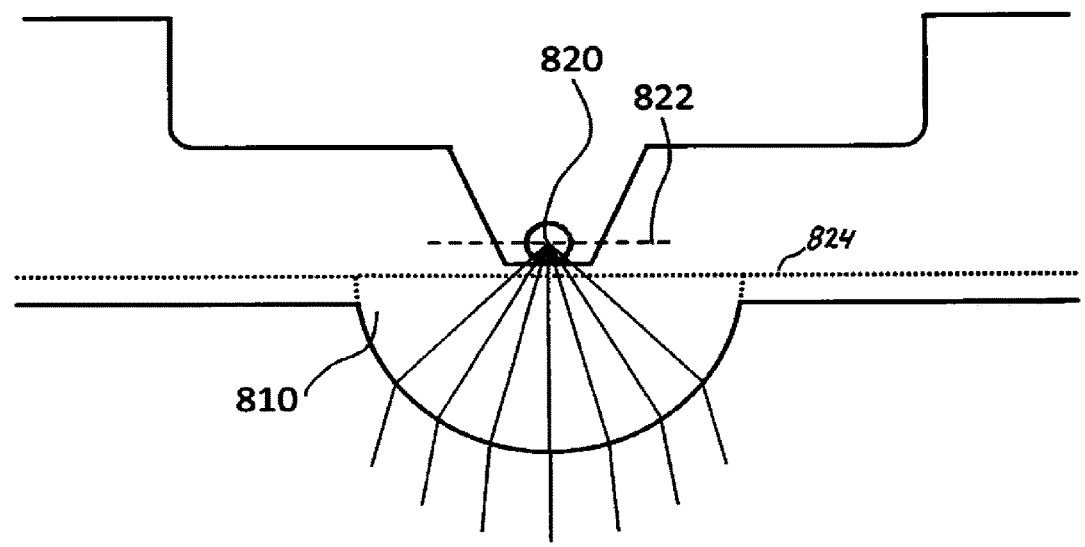

FIGS. 7, 8A and 8B illustrate embodiments of a focal lens for a tray according to the invention. FIG. 7 illustrates rays emanating from the center of the hemisphere. FIGS. 8A and 8B illustrates how rays originating at the aplanatic point pointing in a wide arc of directions are collected after passage through a hemispherical focal lens so that a large numerical aperture of the combined optical system can be achieved.

Figure 9:
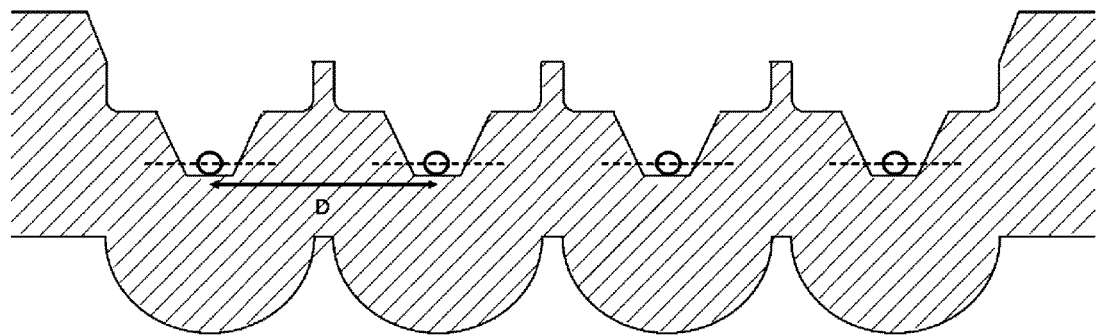
Figure 10:
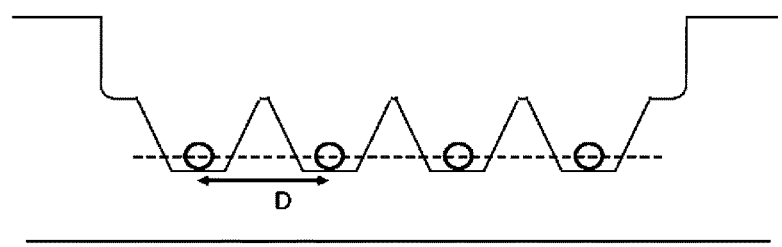

FIGS. 9 and 10 illustrate a comparison between an embodiment of a tray according to the present invention (FIG. 9) and a tray according to the prior art (FIG. 10), notably with regard to a transverse distance D between neighbouring accommodating zones.

Figure 11:
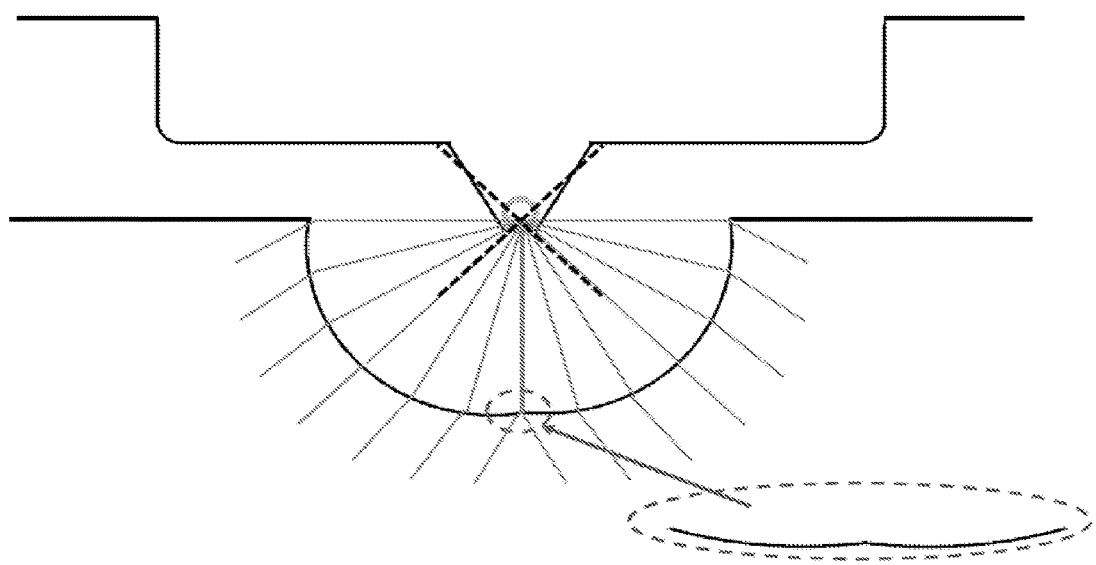

FIG. 11 illustrates a tomographic reconstruction of a dual lens in an embodiment of a tray according to the present invention.

Figure 12:
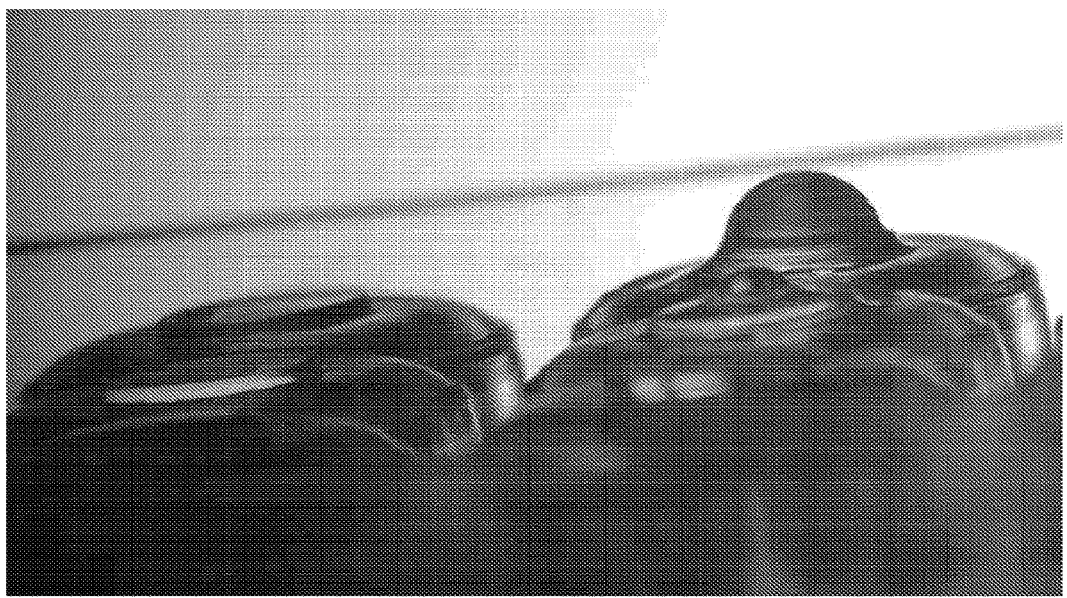

FIG. 12 is a photograph of an embodiment of a tray according to the invention.

Figure 13:

FIG. 13 shows images obtained through the bottom of the tray of FIG. 12.

Figure 14:
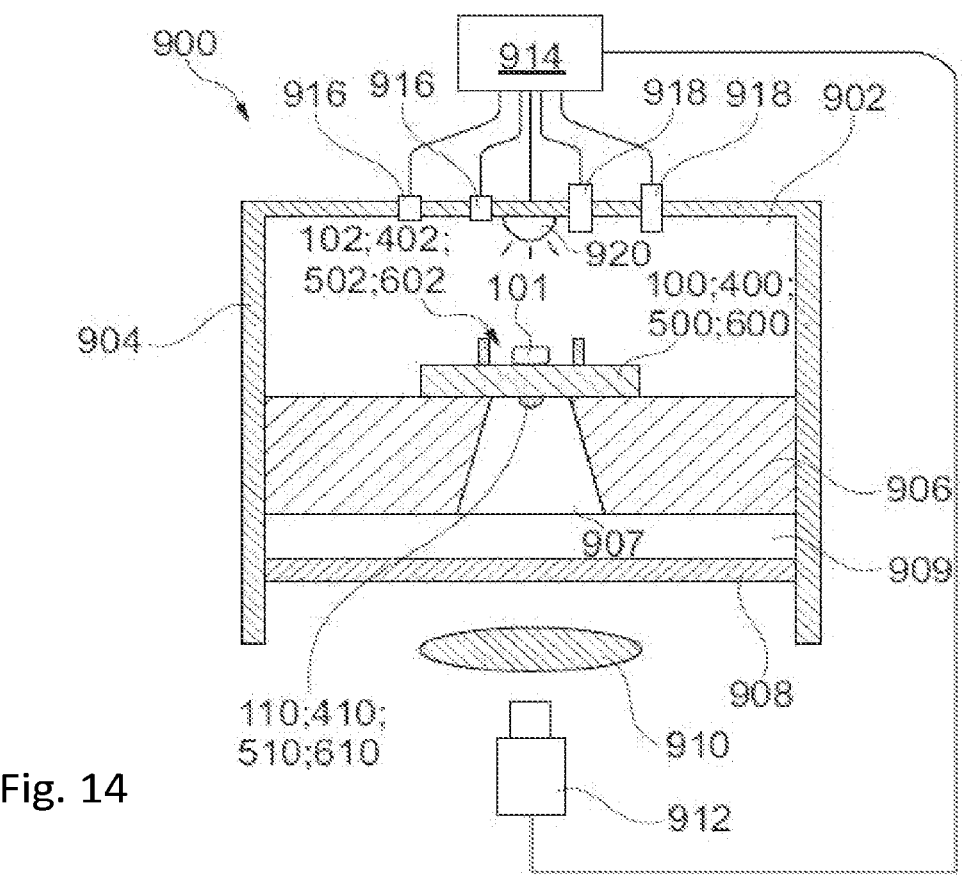
Figure 15:
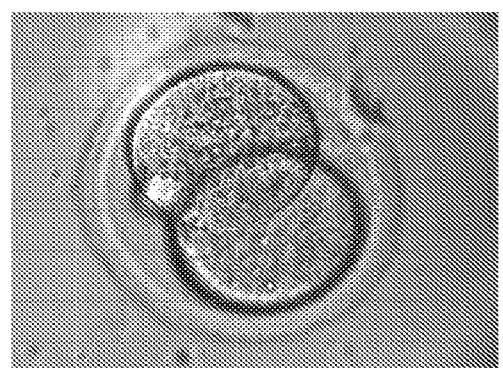

FIG. 14 shows an embodiment of a system according to the invention;

FIG. 15 is an exemplary photo of an embryo taken at an early stage of in vitro fertilization. The image was acquired through a tray according to the first aspect of the invention as claimed and described herein with a hemispherical glass lens attached to the bottom (radius 1.0 mm) as shown in principle in FIG. 5

Figure 2:
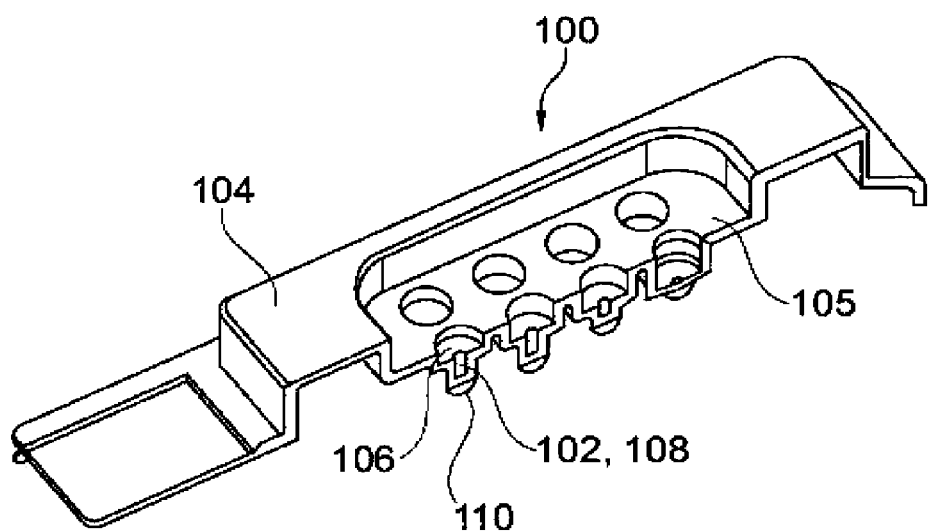
FIG. 2 shows a perspective cut of the tray of FIG. 1; In this particular representation 100: 104 upper surface, 105 large area to be filled with immersion oil to avoid evaporation. 106 large wells filled with growth medium with a central accommodating microwell, 102 and 108 of various depths. 110 hemispherical focal lens attached to the bottom of the well.

The tray 100 of FIG. 1 comprises a plurality of accommodating zones 102 for accommodating respective cell cultures, such as embryos. In the embodiment shown, a total of 12 accommodating zones are provided in a two-dimensional 3×4 matrix pattern. The accommodating zones are provided by a carrier structure 104 formed, e.g., from injection moulded plastics. As shown in FIG. 2, each accommodating zone 102 is formed in a depression 106, which in turn is provided in a recessed area 105 of the carrier structure 104. An indent 108 (i.e. micro-well) is formed in each depression 106 (i.e. well). The accommodating zone is at the bottom of the indent 108 The depressions and indents may be shaped and sized as disclosed in WO 2009/003487, which is hereby incorporated by reference. A focal lens 110 integrally formed with or bonded to the carrier structure 104 is placed at the bottom surface beneath each indent 108, the focal lens 110 being provided at an outer surface of the carrier structure, i.e. at the downwardly facing outer surface of a well formed by each depression 106 and indent 108. In use, respective cell cultures, such as embryos for in vitro fertilization are positioned in the indents 108, and the cell cultures are subsequently cultured in an appropriate environment, such as an incubator. A culture medium is preferably provided in the depressions 106, and the indents 108, thus filling the accommodating zone along with the cell culture, as generally disclosed in WO 2009/003487. The general recess 105 is filled with an immersion oil to avoid osmotic stress due to evaporative loss of media. The carrier structure 104 may be integrally moulded from a transparent plastics material. Each focal lens 110 may be integrally moulded with the carrier structure, i.e. formed in one piece with the carrier structure, or the focal lenses 110 may be provided as separate elements of, e.g. glass, bonded to a bottom surface of the carrier structure 104.

Figure 3:
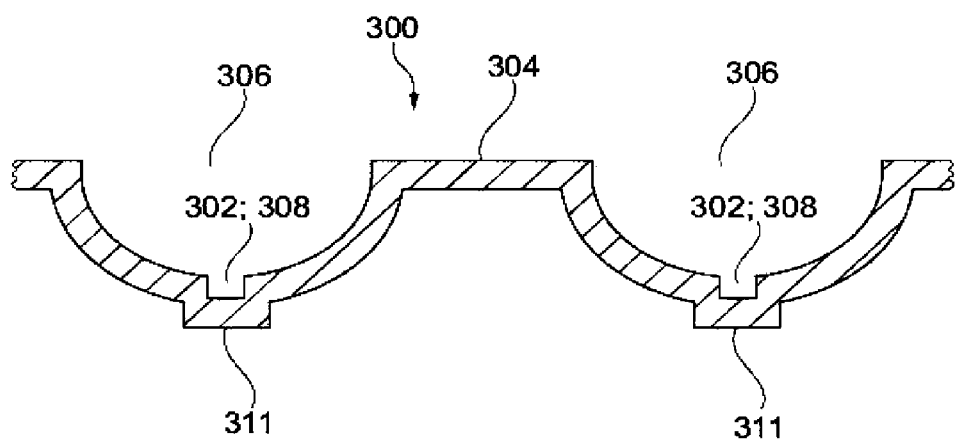
FIG. 3 shows a cross-section of a tray according to the prior art; Note the planar bottom 302,308 of the central accommodating microwell and the planar bottom surface, 311, which does not constitute a focal lens as it is not a focusing lens does not magnify the cell culture and is not improving the numerical aperture of the system.

FIG. 3 illustrates a prior art tray 300 according to the principles of WO 2009/003487. The tray 300 comprises a number of tray accommodating zones 302 formed in a carrier structure 304. Each accommodating zone 302 is formed by an indent 308 at the bottom of a depression 306 in the carrier structure 304. The tray 300 is configured for being accepted by an incubator, in which cell cultures accommodated in the indents 308 are cultured. Monitoring of the cell cultures is performed by means of a microscope arranged below the carrier structure 304 and receiving light rays through the carrier structure 304 and its substantially planar lower surface 311 at the bottom of each indent 308.

A first embodiment of a tray 400 according to the invention shown in FIG. 4 comprises a carrier structure 404 and a plurality of depressions 406 in the carrier structure. In each depression, an indent 408 is provided, the indent hence forming an accommodating zone 402 for accommodating a cell culture during culturing thereof in, e.g., an incubator. Facing each accommodating zone 402 at an outer (lower) surface of the carrier structure 404, a focal lens 410 is provided at the carrier structure 404. An optional circumferential wall 412 may be provided around each lens 410 to protect the latter against scratches and abrasion during handling on solid surfaces. Alternatively a common wall may protect a series of lenses or constitute an outer rim for the carrier structure to rest upon. The focal lens 410 provides a collection of light rays from the accommodating zone 402, thereby enhancing the magnification visible through a microscope (not shown) and the optical resolution when looking at the cell culture in the accommodating zone from below through the lens 410. A cell culture 101, such as an embryo, is accommodated in the accommodating zone 402. The lens 410 is configured such that a focal plane 411 of the lens extends through the cell culture, i.e. through the indent 408 forming the accommodating zone 402, either along a bottom surface thereof or, as shown in FIG. 4, at a predetermined height above the bottom surface of the indent (i.e. microwell) 408.

A further embodiment of a tray 500 according to the invention shown in FIG. 5A comprises a carrier structure 504 and a plurality of depressions 506 in the carrier structure. As in the embodiment of FIG. 4, an indent 508 is formed in each depression 506, the indent hence constituting an accommodating zone 502 for accommodating a cell culture. At an outer surface of the carrier structure 504 and facing each accommodating zone 502, i.e. at a lower surface of the carrier structure 504, a focal lens 510 is bonded to the carrier structure 504. The focal lens 510 constitutes an element separate from the carrier structure 504, the lens 510 being bonded to the carrier structure 504 by any suitable means, such as gluing, etching, press-fitting or by a combination of the aforementioned techniques. The focal lens 510 may be made from the same material as the carrier structure 504 or by a different material. In one embodiment, the carrier structure 504 is moulded from a plastics material, and the lens 510 is formed from the same plastics material. Alternatively, the focal lens 510 may be shaped from glass or another transparent material with desirable optical properties. A circumferential wall 512 is provided around the lens 510 to protect the latter against scratches and abrasion during handling on solid surfaces. Alternatively a common wall may protect a series of lenses or constitute an outer rim for the carrier structure to rest upon. The focal lens 510 provides a collection of light rays from the accommodating zone 502, thereby enhancing the magnification visible through a microscope (not shown) and the optical resolution when looking at the cell culture in the accommodating zone from below through the lens 510. The lens 510 is configured such that a focal plane 511 or 513 of the lens extends through the cell culture, i.e. through the indent 508 forming the accommodating zone 502, either along a bottom surface thereof or at a predetermined height above the bottom surface of the indent (i.e. microwell) 508.

In the embodiments of FIGS. 4 and 5A alike, each of the lenses 410 and 510 has a first diameter $D_L$ at its interface with a surface 414 and 514 defined by a part of the carrier structure 404 and 504 surrounding the lens 410 and 510. The accommodating zone 402 and 502 formed by indents 408 and 508 has a second diameter $D_Z$. In preferred embodiments of the invention, the accommodating zone diameter $D_Z$ is smaller than lens diameter $D_L$ in order to ensure that the lens provides sufficient magnification and visibility of the entire surface area of the accommodating zone 402 and 502, i.e. of the bottom surface of the indent 408 and 508. The optimal position and curvature of the focal lens surface relative to the accommodating zone depends on the optical properties of the materials and media involved. In one embodiment the optimal position of the accommodating zone is close to the center of the hemisphere (see FIG. 7). In another preferred embodiment the optimal position of the accommodating zone is close to the aplanatic point of the hemisphere FIG. 5B shows an alternative configuration of a microwell being concavely curved for accommodation of a cell culture. The tray 540 of FIG. 5B comprises carrier structure 544, depression 546, indent 548 forming accommodating zone (i.e. microwell 542) forming a curved bottom surface 543. The curved bottom surface 543 may facilitate correct positioning of the cell culture (not shown in FIG. 5B) relative to focal lens 550. The focal lens 550 is protected by wall(s) 552.

The respective structures shown in FIGS. 4, 5A and 5B may be incorporated in or form part of the embodiment of a tray 100 as shown in FIGS. 1 and 2. Hence, each one of the carrier structures 404, 504 and 544 may be identical to the carrier structure 104. The depressions 406, 506 and 504, indents 408, 508 and 548, accommodating zones 402, 502 and 542, and focal lenses 410, 510 and 550 may be formed identically as the like elements depicted in FIGS. 1 and 2, i.e. like the depressions 106, indents 108, accommodating zones 102 and focal lenses 110.

FIGS. 6A-6C illustrate further embodiments of a tray 600 according to the invention. The tray comprises a plurality of accommodating zones 602 formed in a carrier structure 604, each of the accommodating zones 602 being sized to accommodate a cell culture during culturing, such as incubation thereof. The accommodating zones 602 may suitable be formed by depressions in the carrier structure, and optionally separated by walls or protrusions from the carrier surface as indicated on the figure. A common focal lens 610 is provided at a lower surface of the carrier structure 604. The focal lens 610 is sized to cover a plurality of accommodating zones 602 in order to allow the cell cultures in the plurality of accommodating zones 602 to be viewed through one single lens 610. In one embodiment, the tray 600 comprises only one focal lens 610, whereas in other embodiments the tray 600 comprises a plurality of focal lenses 610, each of which is sized to cover a plurality of accommodating zones 602.

The focal lens(es) 610 may be integrally formed with the remainder of the carrier structure 604, such as by injection moulding of the carrier structure 604 and the focal lens(es) 610 together from a single piece of material. Alternative, the focal lens or lenses 610 may be provided as one or more separate elements affixed to a surface of the carrier structure, the focal lens or lenses 610 being made from the material of the carrier structure 604 or from another transparent material.

As shown in FIGS. 6A-6C, in particular in FIG. 6B, the carrier structure may form a barrier wall between neighbouring accommodating zones 602 for preventing accidental transfer of a cell culture from one accommodating zone to a neighbouring accommodating zone or unintentional exchange of cell cultures between accommodating zones.

FIGS. 7, 8A and 8B show alternative embodiments of a focal lens for use in embodiments of the present invention. The lens 710 of FIG. 7 show tracing of rays emanating from the central point within the hemisphere (illustrated by arrows in FIG. 7). The rays emerge from a center point 720 of the lens 710 at a feature plane 722, which coincides with the planar surface 724 of the lens. The respective focal lenses 810 of FIGS. 8A and 8B collect optical rays emerging from the aplanatic point 820 in a feature plane 822, which is offset from the planar surface 824 of the lens 810.

Any one of the lenses 710 and 810 of FIGS. 7, 8A and 8B may constitute a focal lens in the aforementioned embodiments of FIGS. 1, 2, and 4, 5A, 5B, and 6A-6C, i.e. any one of the lenses 110, 410, 510, 550 and 610.

A preferred embodiment of the invention the optimal position of the accommodating zone is close to the aplanatic point of the hemisphere as illustrated in FIGS. 8A and 8B.

FIGS. 9 and 10 illustrate a comparison between an embodiment of a tray according to the present invention (FIG. 9) and a tray according to the prior art (FIG. 10). The tray according to the invention of FIG. 9 includes a focal lens associated with each accommodating zone. The distance between neighbouring accommodating zones, in the cross-sectional plane, is indicated by dimension D in FIG. 9. The prior art tray of FIG. 10 has a flat bottom surface. Like in FIG. 9, the distance between neighbouring accommodating zones is indicated by dimension D in FIG. 10. It will be noted that the distance D is smaller in FIG. 10 than in FIG. 9. This is due to the fact that, in the prior art, for the acquisition of a satisfactory image by means of an optical system (not shown), including e.g. a microscope and a camera, the cell cultures must be provided at relatively small mutual distances in order to allow a camera to acquire images of multiple accommodating zones at a time. This in turn has the disadvantage that positioning into and/or picking of cell cultures from the accommodating zones, e.g. following selection of an embryo for transfer, is rendered difficult, in particular in systems, in which such positioning and/or picking is carried out manually. The tray according to the invention, one embodiment of which is depicted in FIG. 9, overcomes that disadvantage thanks to the focal lens providing magnification of the cell culture within the accommodating zone, as one single image can be acquired of a plurality of accommodating zones at a time without compromising image quality. Generally, the magnification provided by the focal lens reduces the need for precision during handling of the tray and/or of the cell cultures.

FIG. 11 illustrates a dual lens tomographic reconstruction in an embodiment of a tray according to the invention.

FIG. 12 is a photo of a tray according to an embodiment of the invention. To the left side, the tray of FIG. 12 comprises a conventional well with a flat/planar bottom. To the right, a well with an attached hemispherical glass lens with a radius of 1.0 mm is provided. The overall design is similar to the concept in FIG. 5A.

The photo in FIG. 13 shows a view from beneath showing an approximately 3 times magnification of the bottom of the central micro well (left without focal lens; right with focal lens). The right well with attached focal lens was used to acquire the image in FIG. 15.

FIG. 14 shows an embodiment of a system 900 according to the invention. The system may e.g. constitute or form part of an in vitro fertilization apparatus for culturing embryos. The system 900 comprises a culturing chamber 902, such as an incubating chamber, and a control system 914 for maintaining a controlled incubating environment in the culturing chamber 902. The controlled environment may e.g. be controlled to maintain a predetermined temperature and a predetermined concentration of one or more specific gasses, such as oxygen and carbon dioxide in the culturing chamber. A tray 100, 400, 500, 600 according to the invention is provided within the housing, with a cell culture 101, such as an embryo, accommodated in an accommodating zone 102, 402, 502, 602 of the tray 100, 400, 500, 600. The culturing chamber 902 is encapsulated by walls 904 and a transparent bottom wall 908 made from, e.g., glass or plastics. Within the culturing chamber 902, tray 100, 400, 500, 600 rests on an temperature stabilizing element 906, such as a heated aluminium plate to provide thermostasis, with the optical lens 110, 410, 510, 610 integrally formed with the tray 100, 400, 500, 600 exposed in a passage 907 through the temperature stabilizing element 906. An air gap 909 is provided between temperature stabilizing element 906 and transparent wall 908 to optionally allow for movement of either tray or microscope. Various sensors 916, such as temperature and gas concentration sensors, are provided within the culturing chamber 902 and operatively connected to the control system 914. Control devices 918 are provided for adjusting various parameters of the controlled environment in the culturing chamber 902. The control devices 918 may e.g. include controlled heating and/or cooling elements, or oxygen, nitrogen, or carbon dioxide supply units. The temperature sensors 916 and temperature control devices 918 may also be incorporated in the temperature stabilizing element 916 (This configuration constitute an alternative embodiment that is not shown). A light source 920 is connected to the control system to illuminate the culturing chamber 902 whenever it is desired to acquire an image of the cell culture 101 by means of an optical inspecting unit, including camera unit 912 and optional objective and/or microscope 910. When no image is being captured, the light source is not activated to keep the culturing chamber at darkness. Operation of the inspecting unit is preferably controlled by the control system 914.

FIG. 15 is an exemplary photo of an embryo at an early stage of in vitro fertilization. The image was acquired through a tray according to the first aspect of the invention as claimed and described herein with a hemispherical glass lens attached to the bottom (radius 1.0 mm) as shown in principle in FIG. 5A.

Example 1

Materials

A standard injection moulded polystyrene embryo culture slide (EmbryoSlide™, Unisense FertiliTech A/S, Aarhus, Denmark) resembling the design shown in FIG. 1 and FIG. 2. Except the indentation 102, the microwell, was smaller than shown in the figure i.e. 0.3 mm deep and 0.3 mm in diameter. Hemispherical glass lenses with a radius of 1.0 mm (Edmond optics, UK) was glued onto the bottom surface of some of the wells in the culture slide with cyanoacrylate glue as indicated in by the object 110 in FIG. 2. Some of the wells were left without attached lenses for comparison. The optical performance of the construct was investigated and documented using an inverted microscope and a dissection scope both from (Leica, Wetzlar, Germany).

Optical resolution was investigated using frozen murine 1-cell embryos purchased from (EmbryoTech, California, USA). The Embryos were thawed and handled according to the specifications by the supplier. The embryos were cultivated at 37 degC in Global media (LifeGlobal, USA) at 5% $CO_2$ until the two cell stage was reached. Embryos were placed in media filled neighbouring micro-wells in the EmbryoSlide pre-equilibrated overnight at 37 degC and 5% $CO_2$ and overlaid with IVF approved mineral oil (LifeGlobal, USA).

Some of the embryos were placed in wells with attached micro lenses and others placed in neighbouring wells without lenses.

Results

FIG. 12 shows a side view of the modified EmbryoSlide™ with attached microlenses. The wells to the left are conventional unmodified wells with a flat/planar bottom. The wells to the right include an attached hemispherical glass lens with a radius of 1.0 mm (most distant well on the right in FIG. 12). The attached lenses protrude down below the culturing vessel. They are thus exposed to scratches and abrasion and may therefor be protected by a wall, such as element 412 depicted in FIG. 4.

FIG. 13 shows images obtained through the bottom of the EmbryoSlide™. The well to the left does not contain any modification, i.e. it presents a prior art well, whereas the well to the right is viewed through the attached hemispherical lens, i.e. it present a tray according to the present invention. The accommodating zone i.e. the bottom of the microwell is readily visible and magnified approximately 3.2 times.

The magnification can be utilized in different ways: A) to obtain an optical system with a higher optical resolution due to an increased numerical aperture as described in this invention. B) a reduced need for high magnification by the rest of the optical system. It is thus possible to use a microscope objective with a lower magnification to examine the tray (e.g. 10× instead of 20× objective) and such lower magnification objectives usually have a longer work distance and are thus easier to accommodate in an instrument construct. C) positioning of the tray with the magnified embryo image is less critical as a small displacement of e.g. 3 μm will only result in a displacement of 3 μm/3.2≈1 μm displacement on the embryo image structures.

An example of an image of a live 2-cell murine embryo acquired through the resulting system is shown in FIG. 15. Upon comparison with similar images of the neighbouring wells it is apparent that more details are visible in the image with the focus lens attached.

It should be mentioned that the physical construct is not ideal for imaging as the embryos were not positioned at the aplanatic point for the glass lenses but quite a bit above this point due to the bottom thickness of the EmbryoSlide™.

CONCLUSION

The empirical investigation of the system with attached focus lens supported the principles and expectations outlined in this application. Incorporating a focus lens in the culture vessel can provide images with improved resolution, allow for more flexible designs using less expensive objectives, providing longer working distance, and being more resilient to unavoidable position deviations. The magnification can also be used to obtain high resolution images of embryos placed in different accommodation zones with a single camera system while allowing sufficient displacement and physical barriers between the embryos to avoid any accidental mix-up.

The invention claimed is:

1. A tray for accommodating a cell culture for use during culturing thereof and/or for optical imaging of the cell culture, the tray comprising a carrier structure defining at least one accommodating zone for accommodating the cell culture; characterised in that the carrier structure comprises at least one focal lens, which is integrally formed with or bonded to the carrier structure, the at least one focal lens being arranged to collect light rays emanating from the at least one accommodating zone so as to facilitate imaging of the cell culture through the focal lens and the carrier structure, a diameter of the focal lens exceeding a diameter of the at least one accommodating zone.

2. A tray according to claim 1, wherein the at least one focal lens comprises a transparent structure with at least one curved or symmetrically structured surface.

3. A tray according to claim 1, wherein the at least one focal lens increases the numerical aperture of an optical system inspecting the at least one accommodating zone through the carrier structure.

4. A tray according to claim 1, wherein the at least one focal lens is formed from and integrally moulded with the material forming the carrier structure at the at least one accommodating zone.

5. A tray according to claim 4, wherein the at least one focal lens and the carrier structure are made from a thermoplastic material.

6. A tray according to claim 1, wherein the at least one focal lens is provided as a separate element from a material other than the material forming the carrier structure at the at least one accommodating zone, and wherein the at least one focal lens is embedded in or bonded to the carrier structure.

7. A tray according to claim 1, wherein the at least one accommodating zone comprises a plurality of accommodating zones, and wherein each one of the at least one focal lens is sized to cover a single accommodating zone only.

8. A tray according to claim 1, wherein the at least one accommodating zone comprises a plurality of accommodating zones, and wherein a single one of the at least one focal lens is sized to cover at least two of said accommodating zones.

9. A tray according to claim 1, wherein each one of the at least one accommodating zone is formed by an indent in a depression in the carrier structure, the indent having a smaller diameter than the depression, and wherein the at least one focal lens is integrally formed by a curvature of the carrier structure beneath the indent.

10. A tray according to claim 9, wherein a diameter of the focal lens exceeds a diameter of said indent.

11. A tray according to claim 10, wherein the diameter of the indent is between 0.1 and 0.5 mm, and wherein a diameter of the focal lens is larger than 0.8 mm.

\* \* \* \* \*